United States Patent [19]

Salerno

[11] Patent Number: 4,698,242
[45] Date of Patent: Oct. 6, 1987

[54] THERMOPLASTIC ELASTIC ADHESIVE CONTAINING POLYETHER BLOCK AMIDES

[75] Inventor: Catherine E. Salerno, Stirling, N.J.

[73] Assignee: National Starch and Chemical Corporation, Bridgewater, N.J.

[21] Appl. No.: 890,663

[22] Filed: Jul. 30, 1986

Related U.S. Application Data

[62] Division of Ser. No. 764,830, Aug. 12, 1985, abandoned.

[51] Int. Cl.$^4$ ............................ B05D 5/10; B05D 3/02
[52] U.S. Cl. ................................. 427/208.2; 156/229; 427/2; 427/208.6; 427/389.9
[58] Field of Search ..................... 156/330.9, 334, 164, 156/183, 229, 244.11, 244.22, 244.27; 427/208.2, 2, 208.6, 389.9

[56] References Cited

U.S. PATENT DOCUMENTS

| | | | |
|---|---|---|---|
| 4,208,493 | 6/1980 | Deleens et al. | 525/420 |
| 4,230,838 | 10/1980 | Foy et al. | 525/408 |
| 4,242,470 | 12/1980 | Gergen et al. | 525/92 |
| 4,252,920 | 2/1981 | Deleens et al. | 525/430 |
| 4,259,220 | 3/1981 | Bunnelle et al. | 260/27 |
| 4,361,680 | 11/1982 | Borg et al. | 525/420 |
| 4,411,954 | 10/1983 | Butch et al. | 428/343 |
| 4,418,123 | 11/1983 | Bunnelle et al. | 428/517 |
| 4,419,494 | 12/1983 | Puletti et al. | 525/95 |
| 4,505,056 | 3/1985 | Beneteau | 36/117 |
| 4,543,099 | 9/1985 | Bunnelle et al. | 604/385 A |
| 4,610,745 | 9/1986 | Sallee et al. | 156/244.11 |

FOREIGN PATENT DOCUMENTS

| | | | |
|---|---|---|---|
| 2523143 | 9/1983 | France | 525/167 |
| 2533577 | 3/1984 | France | 525/167 |

OTHER PUBLICATIONS

Technical Information Bulletin of ATOCHEM, "PEBAX", Notice No. 18/FEV./84/50 from ATOCHEM S.A.

*Primary Examiner*—Thurman K. Page
*Attorney, Agent, or Firm*—Ellen T. Dec; Edwin M. Szala

[57] ABSTRACT

The invention is directed to thermoplastic hot melt adhesive compositions which function as elastic bands for disposable items.

8 Claims, No Drawings

4,698,242

THERMOPLASTIC ELASTIC ADHESIVE CONTAINING POLYETHER BLOCK AMIDES

This application is a division of application Ser. No. 764,830, filed Aug. 12, 1985, now abandoned.

BACKGROUND OF THE INVENTION

Elasticized leg and waist bands have gained increasing popularity in the areas of disposable applications, such as disposable diapers, incontinent pads and hospital gowns. A commercially viable approach for use on high speed production equipment was developed by Buell and disclosed in U.S. Pat. No. 4,081,301. According to this method, continuous bands of elastic, maintained in a stretched position, are glued or heat sealed onto the continuous web from which the disposable diapers are made.

Recognizing that greater efficiency could be achieved if the adhesion of the elastic band to the substrate did not require a separate adhesive or heating means, attempts have been made to prepare adhesives which exhibit the required degree of elasticity without sacrificing the necessary adhesive and cohesive properties. In U.S. Pat. No. 4,259,220, Bunnelle et al. proposed viscoelastic hot melt pressure sensitive compositions prepared from a rubbery block copolymer containing a rubbery polyisoprene midblock portion and a plurality of crystalline poly(vinylarene) endblocks; and two different resins, one of which is a tackifying resin compatible with the midblock and the other a reinforcing resin for the endblock portion of the copolymer.

SUMMARY OF THE INVENTION

The present invention is directed to thermoplastic hot melt adhesive compositions which function as elastic bands for disposable items and particularly for leg or waist band closures on disposable diapers. In particular, the present invention discloses a hot melt pressure sensitive adhesive prepared from (a) a rubbery block copolymer containing a rubbery polyisoprene midblock portion and a plurality of crystalline poly(vinylarene) endblocks; (b) a tackifying resin compatible with the midblock portion; (c) polyether block amide, and (d) an antioxidant.

The resulting adhesives possess exceptional elastic memory, high tensile strength and, in particular, are characterized by excellent peel adhesion to the polyethylene and nonwoven substrates generally used for disposable applications. While not wishing to be bound by theory, it is believed that these properties are achieved from the inherent adhesive strength contributed by the high molecular weight polyether block amide polymer to the entire hot melt adhesive system rather than by a mere reinforcement of any portion of the block copolymer.

DETAILED DESCRIPTION OF THE PREFERRED EMBODIMENTS

The primary component of the adhesive compositions used in the present invention are block copolymers having the general configuration:

A-B-A or A-B-A-B-A-B- wherein the polymer blocks A are non-elastomer polymer blocks which, as homopolymers have glass transition temperatures above 20° C., while the elastomeric polymer blocks B are isoprene. Further, they may be linear or branched. Typical branched structures contain an elastomeric portion with at least three branches which can radiate out from a central hub or or can be otherwise coupled together.

The non-elastomeric blocks which make up approximately 17 to 75%, by weight of the block copolymer may comprise homopolymers copolymers of vinyl monomers such as vinyl arenes, vinyl pyridines, vinyl halides and vinyl carboxylates, as well as acrylic monomers such as acrylonitrile, ethacrylonitrile, esters of acrylic acids, etc. Monovinyl aromatic hydrocarbons include particularly those of the benzene series such as styrene, vinyl toluene, vinyl xylene, ethyl vinyl benzene as well as dicyclic monovinyl compounds such as vinyl naphthalene and the like. Other non-elastomeric polymer blocks may be derived from alpha olefins, alkylene oxides, acetals, urethanes, etc. Styrene is preferred.

Typical of the rubbery block copolymers useful herein are the polystyrene-polyisoprene-polystyrene types containing at least 17% styrene which may be prepared using methods taught, for example, in U.S. Pat. Nos. 3,239,478; 3,427,269; 3,700,633; 3,753,936; and 3,932,327. Alternatively, they may be obtained from Shell Chemical Co. for example under the tradename Kraton D1111 or from Phillips under the tradename Solprene 423. If desired, a portion of these high styrene containing copolymers can be replaced by those of lower styrene contents as, for example, Kraton 1107 or Kraton 1117 in order to adjust the melt indeces for use on various manufacturing equipment. In formulating adhesives for use herein, the block copolymer should be used in an amount of 35 to 75%, preferably 40 to 60%, by weight of the adhesive.

The tackifying resins which are present in the hot melt adhesive used herein serve to extend the adhesive properties of the block copolymer. As contemplated, the term "tackifying resin" comprise on any tackifying resin compatible with the isoprene midblock and includes: (1) polyterpene resins having a softening point, as determined by ASTM method E28 58T, of from about 60° to 140° C. the latter polyterpene resins generally resulting from the polymerization of terpene hydrocarbons, such as the bicyclic mono-terpene known as pinene in the presence of Friedel-Crafts catalysts at moderately low temperatures. (2) phenolic-modified terpene resins such, for example, as the resin product resulting from the condensation in an acidic medium, of a bicyclic terpene and a phenol; (3) aliphatic petroleum hydrocarbon resins having a Ball and Ring softening point of from about 60° to 140° C., the latter resins resulting from the polymerization of monomers consisting primarily of olefins and diolefins; and (4) hydrogenated copolymers of alpha-methyl styrene and styrene having a softening point of about 78° to 125° C.

Especially preferred are resins which are polymerized from a stream of aliphatic petroleum derivatives in the form of dienes and mono-olefins having 5 or 6 carbon atoms generally in accordance with the teachings of U.S. Pat. No. 3,577,398. The resulting solid hydrocarbon resin consists essentially of polymerized structures derived from these aliphatic dienes and mono-olefins of 5 or 6 carbon atoms and since the dienes are more reactive, at least 40 percent by weight and preferably a major proportion of said structures are derived from the dienes. In this type of resin, the dienes are piperylene and/or isoprene. However, in some formulations, the percentage of isoprene is extremely low. In the solid resin of this embodiment the molecular weight may range between about 900 and 1300 with the mean number average molecular weight being about 1100. This solid resin also has a softening point in the neighborhood of 100° C. In one preferred form, i.e., Wingtack 95 offered by Goodyear Chemical Company, the softening point is 95° C. These tackifying resins are present in an amount of 10 to 45, preferably 20 to 40% by weight of the adhesive.

The polyether block amides used herein are, more specifically, polyether-ester-amide sequence copolycondensates containing chains consisting of recurrent units with the formula

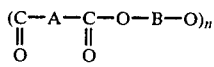

where
- A is the polyamide sequence resulting from the loss of two carboxylic functions from the dicarboxylic polyamide;
- B is the polyoxyalkylene glycol sequence resulting from the loss of the two hydroxylated groups at the chain-ends of the polyoxyalkylene glycol, and n is the number of recurrent units forming the sequence copolycondensate chain.

More specifically the copolycondensate is a product obtained from copolymerization of a $\alpha,\beta$-dicarboxylic polyamide or copolyamide having a molecular weight comprised between 300 and 15,000, preferably between 800 and 5,000, amounting to 95 and 15% by weight and a $\alpha,\beta$-dihydroxy aliphatic polyoxyalkylene having a molecular weight of 100 to 6,000, preferably between 200 to 3,000, amounting to 5 to 85% by weight, the said product having a melting point between 80° and 210° C., and preferably between 100° and 150° C., and a molten state viscosity of 10 to 2,000 Pa. sec. at 200° C.

Preferred copolycondensates for use herein are the polyetheresteramide sequences formed from a prepolymer of caprolactam, dodecalactam and adipic and condensed with polyoxypropyleneglycol; a prepolymer of caprolactam, 11-amino-undecanoic acid and adipic acid condensed with polyoxytetramethyleneglycol and polyoxypropylene glycol; or a prepolymer of dodecalactam and adipic acid condensed with polyoxytetramethyleneglycol.

These polyether ester amide copolycondensates may be prepared using the methods described in U.S. Pat. Nos. 4,208,493, 4,230,838; 4,252,920; and 4,361,680, the disclosures of which are included herein by reference. Alternatively, the polyether amide may be obtained from ATO Chimie under the tradename Pebax. The Pebax polymers having a melting point less than about 150° C. have been found to be preferred for use herein. Particularly useful is the grade designated Pebax 5562 MNOO which has a melting point of 120° C., a shore hardness of 55D and a specific gravity of 1.06. This material is believed to be a polyetheresteramide formed from a prepolymer of caprolactam, dodecalactam and adipic acid condensed with polyoxypropylene glycol. The poly (ether block amide) copolycondensate is used in the present adhesive in an amount of 5 to 25%, preferably 10 to 20% by weight.

Antioxidants for use herein include high molecular weight hindered phenols and multifunctional phenols such as sulfer and phosphorous-containing phenols. Hindered phenols are well known to those skilled in the art and may be characterized as phenolic compounds which also contain bulky radicals in close proximity to the phenolic hydroxyl group thereof. In particular, tertiary butyl groups generally are substituted onto the benzene ring in at least one of the ortho positions relative to the phenolic hydroxy group. The presence of these radicals in the vicinity of the hydroxyl group serves to retard its stretching frequency and correspondingly, its reactivity. This steric hindrance thus provides the phenolic compound with its stabilizing properties.

Representative hindered phenols include:
1,3,5-trimethyl-2,4,6-tris(3,5-di-tert-butyl-4-hydroxybenzylbenziene; pentaerythrityl tetrakis-3(3,5-di-tert-butyl-4-hydroxy-phenyl)-propionate, n-octadecyl-3(3,5-di-tert-butyl-4-hydroxyphenyl)propionate, 4,4'-methylenebis(2,6-di-tert-butylphenol); 2,2'-methylenebis (4-methyl-6-tert-butylphenol); 4,4'-thiobis(6-tert-butyl-o-cresol); 2,6-di-tert-butylphenol; 6-(4-hydroxyphenoxy)-2,4-bis-(n-octylthio)-1,3,5 triazine; 2,4,6-tris(4-hydroxy-3,5,-di-tert-butylphenoxy)-1,3,5-triazine; di-n-octadecyl-3,5-di-tert-butyl-4-hydroxy-benzylphosphonate; 2-(n-octylthio)ethyl)3,5-di-tert-butyl-4-hyroxy-benzoate, and sorbitol hexa-[3-(,5-di-tert-butyl-4-hydroxy-phenyl)propionate.] The antioxidant and is generally used at levels of 0.2 to 2% by weight.

The performance of these antioxidants may be further enhanced by utilizing, in conjunction therewith (1) synergists such, for example, as thiodipropionate esters and phosphites; and (2) chelating agents and metal deactivators such, for example, as ethylenediamine tetraacetic acid.

Optional additives may be incorporated in minor amounts, generally less than 3% by weight, into the hot melt compositions in order to modify certain properties thereof. Among these additives may be included colorants such as tianum dioxide; fillers such as talc and clay, etc., hydrocarbon process oils; etc.

These hot melt adhesive compositions may be formulated using techniques known in the art. An exemplary procedure involves placing the tackifying resin, polyether block amide, stabilizer and any optional additives whose presence may be desired in a jacketing mixing kettle, preferably in a jacketed heavy duty mixer of the Baker Perkins or Day type, which is equipped with rotors and thereupon raising the temperature to a range of from about 250° to 350° F., the precise temperature utilized depending on the melting point of the particular tackifying resin. When the resin and copolycondensate polymer have melted, stirring is initiated and the block polymer, is added, the addition of the block polymer being extended over a prolonged period in order to avoid the formation of lumps. Mixing and heating are continued until a smooth, homogenous mass is obtained.

In the examples that follow, the adhesive prepared were subjected to the tests described below:

Tensile Strength:
Tensile strength values for the elastic of this invention are used as a measure of cohesive strength. A sample of known thickness is elongated at room temperature using an Instron and the tensile strength at 100% elongation is recorded. Samples having tensile strengths of at least about 35 psi at 100% elongation provide adequate cohesive strength.

Dead Load Deformation:
The term "dead load deformation" or "dead load creep" refers to a measurement of "cold flow" or permanent deformation at one or more fixed test temperatures, e.g., 23° C. or 25° C., 40° or 41° C. and 49° or 50° C. A sample of known length is suspended vertically in a chamber maintained at the test temperature and a mass is attached to the lower (free) end of the sample. The sample is cut to a size such that the force per unit area is 1500 g/cm$^2$. After approximately 3 hours at the test temperature, the sample is removed, the weight is detached, and the sample is allowed to relax under the influence of its own inherent elastomeric forces. The length of the relaxed sample ($L_2$) is compared to the original length ($L_1$) and the "dead load creep" (permanent deformation) is determined according to the formula ($L_2$-$L_1$)/$L_1 \times 100\%$. Values of less than 20% deformation are considered adequate.

T-peel:

Peel adhesion values are determined 24 hours ater formation of the bond between cold-rolled steel plates and the self-adhering elastic. The bond is formed at room temperature by applying a 0.5"×20 mil×3" elastic/adhesive strip onto the steel, backing it with masking tape, and sealing at room temperature using 20 psi pressure for 2 seconds. The bond is tested using an Instron. Values of at least about 4 pounds per linear inch indicate acceptable tack levels for the more stringent leg banding applications, however lower levels are acceptable for lower tension applications such as waist banding.

Polyethylene film and Non Woven peel:

A 20 mil film of adhesive is made using a Carver press at 350° F. under 8,000 lbs. pressure with a residence time of approximately 15 sec. Then 3×½" samples are cut and backed with masking tape. The samples are bonded to non-woven or 2 mil polyethylene film backed with tape using 2 passes with a 4½ lb. roller. The bond is peeled immediately using an Instron at 12"/min. Results are recorded in grams per linear inch.

The following examples will further illustrate the embodiments of the invention. In these examples all parts given are by weight and all temperatures in degrees Celsius unless otherwise indicated.

EXAMPLE 1

Adhesives were prepared in a Sigma mixer heated to 170° C. by blending until homogenous the components in the amounts shown in Table I. The adhesives were then tested as described above with the results also shown in Table I.

TABLE I

| Component | Adhesive 1 | 2 | 3 | 4 |
|---|---|---|---|---|
| Kraton 1111 | 55 | 55 | 55 | 55 |
| Pebax 5562 MN 00 | 15 | 15 | 15 | 15 |
| Wingtack 95 (1) | 30 | — | — | — |
| Nirez V-2150 (2) | — | 30 | — | — |
| Regalrez 1078 (3) | — | — | 30 | — |
| Escorez 5300 (4) | — | — | — | 30 |
| Dead load Deformation | 5% | 5% | 5% | 0% |
| Tensile Strength @ 100% | 37 psi | 117 psi | 37 psi | 56 psi |
| T-peel | 4.4/L.I. | 6.0/L.I. | 2.6/L.I. | 2.0/L.I. |
| Polyethylene peel | 900 | N/T | N/T | N/T |
| Nonwoven peel | >1300 | N/T | N/T | N/T |

(1) A C$_5$ terpene resin from Goodyear Chemical Company
(2) A terpene-phenolic tackifying resin from Reichhold Chemical
(3) A hydrogenated styrene-alpha-methyl styrene resin from Hercules Chemical
(4) A hydrogenated dicyclopentadiene resin from Exxon Chemical
N/T — Not tested

EXAMPLE 2

Other adhesives were prepared using different amounts of the components as well as blends of the rubber copolymers. Compositions and tests results are shown in Table II.

TABLE II

| Component | Adhesive 5 | 6 | 7 | 8 | 9 | 10 |
|---|---|---|---|---|---|---|
| Kraton D-1111 | 55 | 55 | 45 | 45 | 40 | 55 |
| Kraton D-1117 | — | — | 10 | — | — | — |
| Kraton D-1107 | — | — | — | 10 | — | 10 |
| Pebax 5562 1 | 10 | 20 | 15 | 15 | 20 | 15 |
| Wingtack 95 | 30 | 30 | 30 | 30 | 40 | 20 |
| Tensile Strength @ 100% | 35 | 52 | 35 | 35 | 45 | 60 |
| Dead Load Deformation | 0% | 3% | 4% | 8% | 4% | 3% |
| T-Peel | 4.2 | 3.4 | 5.4 | 4.2 | * | 1.4 |

*Substrate failure

In a similar manner, other thermoplastic hot melt adhesives may be prepared using other polyether ester amides including, for example, Pebax 2533 SNOO which has a melting point of 148° C., a shore hardness of 75A and a specific gravity of 1.01 as well as Pebax 5533 SNOO which has a shore hardness of 55D, a melting point of 168° C. and a specific quantity of 1.01. Since these latter Pebax grades have higher melting points than the 5562 MNOO grade, higher processing temperatures will be required and there may consequently be some reduction in tensile strength values due to the thermal effects on the block copolymer components.

Now that the preferred embodiments of the present invention have been described in detail, various modifications and improvements thereon will become readily apparent to those skilled in the art. Accordingly, the spirit and scope of the present invention is to be limited only by the appended claims, and not by the foregoing disclosure.

I claim:

1. A method for imparting elongation resistant gathers to portions of a generally non-elastomeric film, or web substrate which comprises contacting a surface of the substrate with a molten band of a self-adhering elastic composition comprising:
   (a) from 35 to 75% by weight of a rubbery block copolymer containing a rubbery polyisoprene midblock portion and a plurality of crystaline poly (vinylarene) endblocks wherein the poly(vinylarene) portion constitute from 17 to 75% by weight of the copolymers;
   (b) from 10 to 45% by weight of a tackifying resin selected from the group consisting of polyterpene resins having a softening point, as determined by ASTM method E28 58T, of from about 60° to 140° C.; phenolic-modified terpene resins; aliphatic petroleum hydrocarbon resins having a Ball and Ring softening point of from about 60° to 140° C.; and hydrogenated copolymers of styrene and alphamethyl styrene having a softening point of from 78° to 125° C.;
   (c) from 5 to 251 % by weight of polyether ester amide; and
   (d) from 0.2 to 2% by weight of an antioxidant.

2. The method of claim 1 wherein the block copolymer is a polystyrene polyiosprene polystyrene copolymer.

3. The method of claim 2 wherein the polystyrene portion comprises at least 22% by weight of the block copolymer.

4. The method of claim 3 wherein the polystyrene portion comprises approximately 22% by weight of the copolymer.

5. The method of claim 1 wherein the polyether ester amide is a sequence copolycondensate containing chains consisting of recurrent units with the formula:

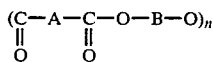

where:

A is the polyamide sequence resulting from the loss of two carboxylic functions from the dicarboxylic polyamide, B is the polyoxyalkylene glycol sequence resulting from the loss of the two hydroxylated groups at the chain-ends of the polyalkylene glycol, and n is the number of recurrent units forming the sequence copolycondensate chain.

6. The method of claim 3 wherein the polyether ester amide is characterized by a melting point of 120° C., a shore hardness of 55D and a specific gravity of 1.06.

7. The method of claim 1 wherein the tackifying resin is a synthetic polyterpene resin having a softening point of 60 to 140° C.

8. The method of claim 1 wherein the polyether ester amide is present in an amount of 10 to 20% by weight of the adhesive.

* * * * *

UNITED STATES PATENT AND TRADEMARK OFFICE
CERTIFICATE OF CORRECTION

PATENT NO. : 4,698,242
DATED : October 6, 1987
INVENTOR(S) : Catherine E. Salerno It is certified that error appears in the above-identified patent and that said Letters Patent are hereby corrected as shown below:

Claim 1, at Col. 6, line 63, "251%" should be -- 25% --.

Signed and Sealed this

Seventeenth Day of January, 1989

Attest:

DONALD J. QUIGG

*Attesting Officer*          *Commissioner of Patents and Trademarks*